United States Patent
Shkolnikov et al.

(10) Patent No.: US 10,845,276 B2
(45) Date of Patent: Nov. 24, 2020

(54) ENZYMATIC SAMPLE PURIFICATION (71) Applicant: Hewlett-Packard Development Company, L.P., Houston, TX (US)

(72) Inventors: Viktor Shkolnikov, Palo Alto, CA (US); Anita Rogacs, San Diego, CA (US)

(73) Assignee: Hewlett-Packard Development, L.P., Spring, TX (US)

( * ) Notice: Subject to any disclaimer, the term of this patent is extended or adjusted under 35 U.S.C. 154(b) by 23 days.

(21) Appl. No.: 15/770,456

(22) PCT Filed: Feb. 29, 2016

(86) PCT No.: PCT/US2016/020137
§ 371 (c)(1),
(2) Date: Apr. 23, 2018

(87) PCT Pub. No.: WO2017/151104
PCT Pub. Date: Sep. 8, 2017

(65) Prior Publication Data
US 2019/0003937 A1   Jan. 3, 2019

(51) Int. Cl.
*C12Q 1/37* (2006.01)
*G01N 1/40* (2006.01)
*C07K 1/34* (2006.01)

(52) U.S. Cl.
CPC .............. *G01N 1/4044* (2013.01); *C12Q 1/37* (2013.01); *C07K 1/34* (2013.01); *G01N 2001/4038* (2013.01)

(58) Field of Classification Search
CPC .......... C07K 1/34; C12Q 1/37; G01N 1/4044; G01N 2001/4038
See application file for complete search history.

(56) References Cited

U.S. PATENT DOCUMENTS 5,085,779 A   2/1992 Crane
5,350,681 A   9/1994 Iacobucci et al.
(Continued)

FOREIGN PATENT DOCUMENTS

CN   101883776   11/2010
EP   0370163     5/1990
(Continued)

OTHER PUBLICATIONS

International Search Report and Written Opinion dated Nov. 23, 2016, PCT Patent Application No. PCT/US2016/020137, filed Feb. 29, 2016, Korean Intellectual Property Office.

*Primary Examiner* — Liban M Hassan
(74) *Attorney, Agent, or Firm* — Rathe Lindenbaum LLP (57) ABSTRACT

An enzymatic purification method involves the introduction of a sample comprising a target analyte and amino acids into a porous matrix of a reaction chamber. The reaction chamber includes first pores and second pores. The first pores contain polypeptide synthesis enzymes that react with the amino acids to form polypeptides. First pores having a first size to be accessible by amino acids but inaccessible by the subsequently formed polypeptides. The second pores have a second size greater than the first size, are in contact with the first pores and form a series extending from within the reaction chamber to a waste chamber. The formed polypeptides are migrated through the series of second pores to the waste chamber. The target analyte of the sample is extracted from the reaction chamber.

16 Claims, 4 Drawing Sheets

(56) References Cited

U.S. PATENT DOCUMENTS

| | | |
|---|---|---|
| 6,509,454 B1 | 1/2003 | Reis |
| 9,062,304 B2 | 6/2015 | Rothberg et al. |
| 9,176,105 B2 | 11/2015 | Mace et al. |
| 2001/0049133 A1 | 12/2001 | McCabe et al. |
| 2004/0115785 A1 | 6/2004 | Fong et al. |
| 2004/0180415 A1 | 9/2004 | Tchaga et al. |
| 2011/0011742 A1 | 1/2011 | Mathers et al. |
| 2011/0250167 A1 | 10/2011 | Boschetti et al. |
| 2012/0129150 A1 | 5/2012 | Carbonell |
| 2012/0321518 A1 | 12/2012 | Ermantraut et al. |
| 2015/0093304 A1 | 4/2015 | Guzman |

FOREIGN PATENT DOCUMENTS

| | | | | |
|---|---|---|---|---|
| GB | 1284925 A | * | 8/1972 | ............. B01J 23/48 |
| WO | WO-2015115993 A1 | | 8/2015 | |

* cited by examiner

ENZYMATIC SAMPLE PURIFICATION

CLAIM FOR PRIORITY

The present application is a national stage filing under 35 U.S.C. § 371 of PCT application number PCT/US2016/020137, having an international filing date of Feb. 29, 2016, the disclosure of which is hereby incorporated by reference in its entirety.

BACKGROUND

Complex Samples, such as blood, serum, cell lysate, extracellular fluid, milk and other biological fluids are often analyzed to identify analytes within the samples or to characterize analytes within the samples. Identifying or characterizing the analytes amongst the multiple molecules of such complex samples is often difficult and time-consuming.

DETAILED DESCRIPTION OF EXAMPLES

Disclosed herein are different examples of enzymatic sample purification systems and methods that utilize enzymes to facilitate faster and less costly preparation of a sample for analysis. Many complex samples such as blood, serum, cell lysate, extracellular fluid, milk and other biological fluids contain degradation products of protein, such as amino acids and peptides, which interfere with the detection and sensing of target analytes in the complex sample. Because the protein degradation products may have sizes and other properties similar to that of many target analytes, separation and removal of such protein degradation products may be difficult. The example enzymatic sample purification systems and methods utilize enzymes that react with protein degradation products to form much larger sized polypeptides. The example enzymatic sample purification systems and methods utilize a porous matrix having differently sized pores. Smaller pores contain polypeptide synthesizing enzymes while entropically retaining target analyte from a received sample within a reaction chamber. Larger pores form a series of pores to form polypeptide passages within the reaction chamber and through which formed polypeptides, resulting from a reaction of the enzymes and protein degradation products, travel to a waste chamber, leaving the purified sample with the target analyte within the reaction chamber for subsequent extraction and analysis. The transport of formed polypeptides to the waste chamber creates a non-equilibrium state in the reaction chamber, enhancing further reaction of the enzymes and remaining protein degradation products. The enhanced reactions form additional polypeptides which continue to travel to the waste chamber through the polypeptide passages in the reaction chamber. The cycle continues for enhanced purification of the sample.

Figure 1:
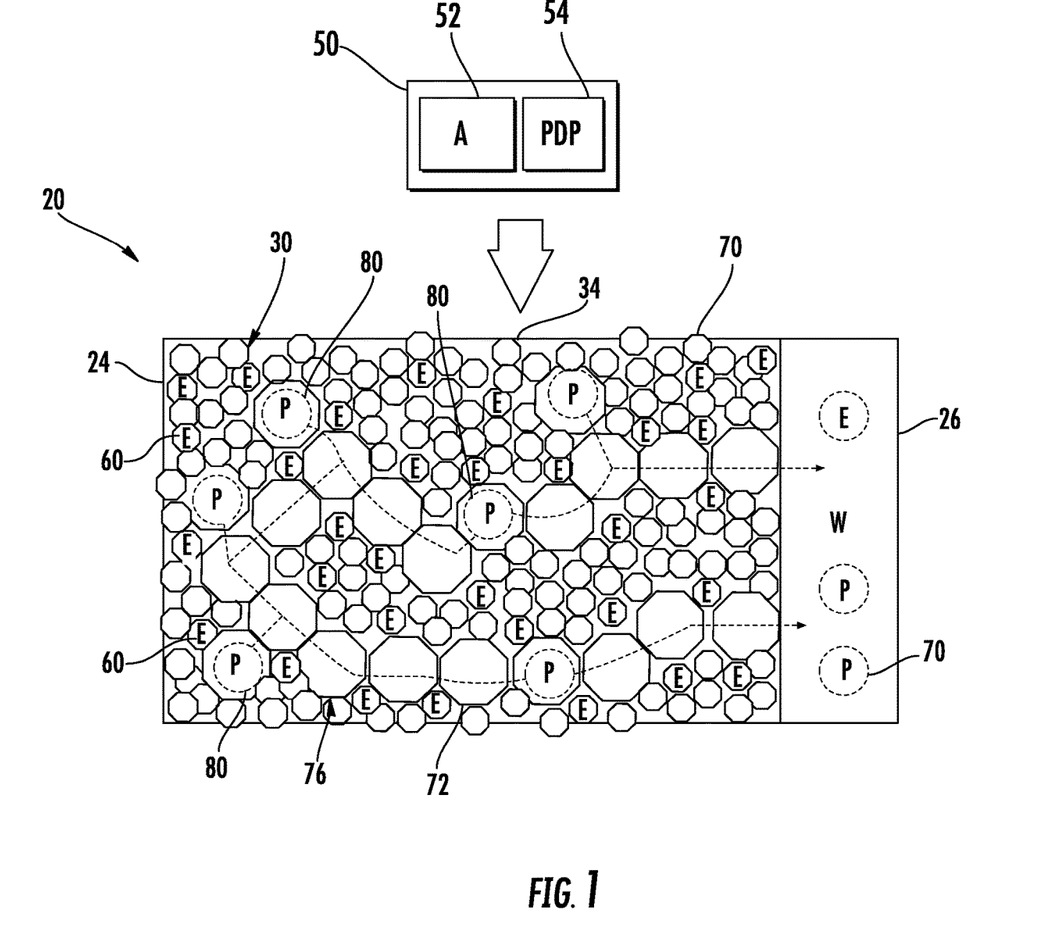
FIG. 1 is a schematic diagram of an example enzymatic sample purification system.

FIG. 1 schematically illustrates an example enzymatic sample purification system 20 which may facilitate faster, less costly and more effective purification of a sample for analysis. System 20 purifies the sample by utilizing polypeptide synthesizing enzymes that react with protein degradation products to form much larger sized polypeptides. As will be described hereafter, system 20 facilitates the continuous migration or transport of formed polypeptides to a waste chamber such that a non-equilibrium state persists within the reaction chamber. The persistent non-equilibrium state within the reaction chamber enhances further reaction of the remaining protein degradation products with the enzymes to form additional polypeptides which are also moved out of the reaction chamber, leaving a more purified sample with its target analyte(s) in the reaction chamber.

To create the persistent non-equilibrium state within the reaction chamber, system 20 utilizes a porous matrix of differently sized pores and a polypeptide passage formed by larger pores of the matrix to facilitate the continuous transport of formed polypeptides out of the reaction chamber and into the waste chamber. At the same time, the number of smaller pores entropically trap or retain the target analyte within the reaction chamber, separated from the polypeptides (and PDP) which have been transported to the waste chamber. Such entropic entrapment is a result of the large number of smaller pores providing much longer, serpentine and maze-like available paths for the smaller target analyte while the larger pores provide a more constrained and more direct path for the movement of the polypeptides to the waste chamber. As shown by FIG. 1, system 20 comprises reaction chamber 24, waste chamber 26 and porous matrix 30.

Reaction chamber 24 comprise a chamber having a port 34 to receive a sample 50 containing a target analyte (A) 52 and a protein degradation product (PDP) 54 (schematically shown). Reaction chamber 24 contains a polypeptide synthesizing enzyme 60 (schematically illustrated in the Figures with "E"). Enzyme 60 is specifically chosen based upon the characteristics of the target analyte 52 in sample 50 to be analyzed. Enzyme 60 specifically chosen so as to react with PDP 54 to formed polypeptides while not reacting with analyte 52 to form polypeptides. Examples of different protein synthesizing enzymes 60 include, but are not limited to, proteases such as pepsin, papain, trypsin, elastase and others. Depending upon the target analyte 60, other polypeptide synthesizing enzymes 60 may be utilized.

In some implementations, reaction chamber 24 may contain other elements such as enzyme cofactors, cosolvents and buffers. Enzyme cofactors are non-protein molecules that catalyze reactions between the enzymes and the PDP 54. Examples of enzyme cofactors include, but are not limited to, cupric ions.

Cosolvents comprise liquid molecules that suspend enzyme 60 and dissolve other substances to form a solution. In one implementation, the cosolvents may be chosen to enhance the reactivity of enzyme 60 with PDP 54. In one implementation, the cosolvents may be organic. In other implementations, cosolvent may be aqueous. Examples of cosolvents include, but are not limited to, glycerol.

Buffers comprise molecules that, as part of the solution, inhibit changes to the pH of the solution. Such buffers may serve as a means of keeping pH at a nearly constant value. Examples of buffers include, but are not limited to, phosphate buffer. Each of the enzyme cofactors, cosolvents, and buffers may be chosen to facilitate thermodynamic conditions favorable for the formation, rather than the breakage of amide bonds to form the polypeptides.

In one implementation, reaction chamber 24 is prefilled with the enzyme 60 as well as enzyme cofactors, cosolvents and buffers, wherein reaction chamber 24 is then "factory sealed" until use. In one implementation, system 20 may be labeled for use with a particular type of sample 50, a particular type of PDP 54 and/or a particular type of target analyte 52, wherein the waste chamber 24 is prefilled with the appropriate amount and relative amounts of a selected enzyme or multiple enzymes 60 as well as respective cofactors, cosolvents and buffers most suitable for the particular type of sample 50, the particular type of PDP 54 and/or the particular type of target analyte 52. As a result, different systems 20 with different combinations of prefilled solution mixes within reaction chamber 24 may be specifically tuned for the exclusion of particular PDPs 54, particular amino acids and/or oligopepetides. Because system 20 may be mass-produced under controlled manufacturing specifications, the task of individual preparing of the enzymatic "cocktail" may be reduced in scope or eliminated, potentially reducing technician error. Moreover, the time and cost associated with individually preparing a solution to purify sample 50 is reduced. Because system 20 is self-contained, system 20 may be adapted for portable applications.

Porous matrix 30 comprises a grid or matrix of a material or multiple materials disposed within or contained within reaction chamber 24. Porous matrix 30 comprises a matrix of internal interconnected spaces or volumes, referred to as cells or pores. In the example illustrated, porous matrix 30 comprises open celled pores 70 and open celled pores 72.

Open celled pores 70 (schematically represented by smaller size octagons) are interconnected to one another and are connected to pores 72. Open celled pores 70 are sized to receive target analyte 52 of sample 50 but to exclude the polypeptides resulting from the reaction of PDP 54 and enzyme 60. Open celled pores 70 are sized so as to be accessible to PDP 54 (the amino acids and oligeopeptides) of sample 50, but inaccessible to the subsequent formed polypeptides. The exact size of pores 70 may be empirically determined and may depend upon particular size characteristics of target analyte 52 of sample 50 as well as the expected size of the polypeptides that will be formed from PDP 54 using enzyme 60 and discharge from reaction chamber 24.

As shown by FIG. 1, pores 70 contain a substantial, if not a majority of enzymes 60. In one implementation, enzyme 60 moved between and amongst the different pores 70. Due to the relatively large number of pores 70, enzymes 60 are entropically trapped within reaction chamber 24.

Open celled pores 72 (schematically represented by the larger octagons) are interconnected to one another and interspersed amongst cells 70. Pores 72 are sized larger than pores 70. Pores 72 are sized at or greater than the anticipated molecular size of the polypeptides that will be formed from the reaction of PDP 54 and enzymes 60. At least some of pores 72 are interconnected to one another so as to form a series or chain of interconnected pores 72. The chain of interconnected pores 72 forms a polypeptide passage 76 extending from the interior of reaction chamber 24 to waste chamber 26. In one implementation, at least one polypeptide passage 76, and in one implementation at least a majority of polypeptide passages 76, extend from waste chamber 26 across at least 50% of a length of matrix 30, and in one implementation across at least 90% of a length of matrix 30, orthogonally away from waste chamber 26, so as to reach more remote regions of matrix 30 distant from waste chamber 26. Each polypeptide passage 76 facilitates the transport of formed polypeptides out of reaction chamber 24 as the polypeptides are created, and into waste chamber 26, facilitating a persistent non-equilibrium state within chamber 24 between the form polypeptides and enzyme 60.

In one implementation, the interconnection of pores 72 to form polypeptide passages 76 is achieved in a random fashion by providing a sufficient density of pores 72 in reaction chamber 24 (the number of pores 72 per unit volume) to increase a likelihood that pores 72 will it be interconnected and will form polypeptide passages 76 that reach to waste chamber 26. In one implementation, pores 70 comprise at least 10% and no greater than 95% of matrix 30, with the remainder comprising pores 72. In yet another implementation, pores 70 comprise at least 80% and no greater than 95% of porous matrix 30.

As the relative number of pores 70 increases with respect to the relative number of pores 72, the likelihood of a larger number of polypeptide passages 76 decreases, possibly slowing the rate at which formed polypeptides may be transported out of reaction chamber 24 to waste chamber 26. However, at the same time, the larger relative number of pores 70 provide matrix 30 with an enhanced ability to entropically trap and retain enzyme 60 as well as the target analyte 52. As will be described hereafter, in other implementations which provide a field to accelerate the transport or movement of polypeptides through passages 76 to waste chamber 26, the enhanced ability of matrix 30 to entropically trap and retain target analyte 52 may allow the strength of the provided field to be stronger to increase the rate at which the polypeptides migrate to waste chamber 26. The relative number of pores 70 and pores 72 may be varied depending upon available time for purification of sample 50 and the degree to which sample 50 is to be purified (the tolerance for small amounts of PDP in the final purified sample 50 extracted from reaction chamber 24).

In other implementations, the connection of pores 72 to form polypeptide passages 76 is achieved under more controlled conditions, wherein the extent to which porous matrix 30 comprises polypeptide passages 76, and possibly even their location or relative locations is more precisely controlled. In one implementation, porous matrix 30 may be formed by free radical polymerization by of monomers (such as, but not limited to methacrylate, and ethyldimethacrylate) in the presence of porogen solvents (such as, but not limited to, methanol and hexane). In other implementations, other methods may be utilized to form porous matrix 30.

Figure 2:
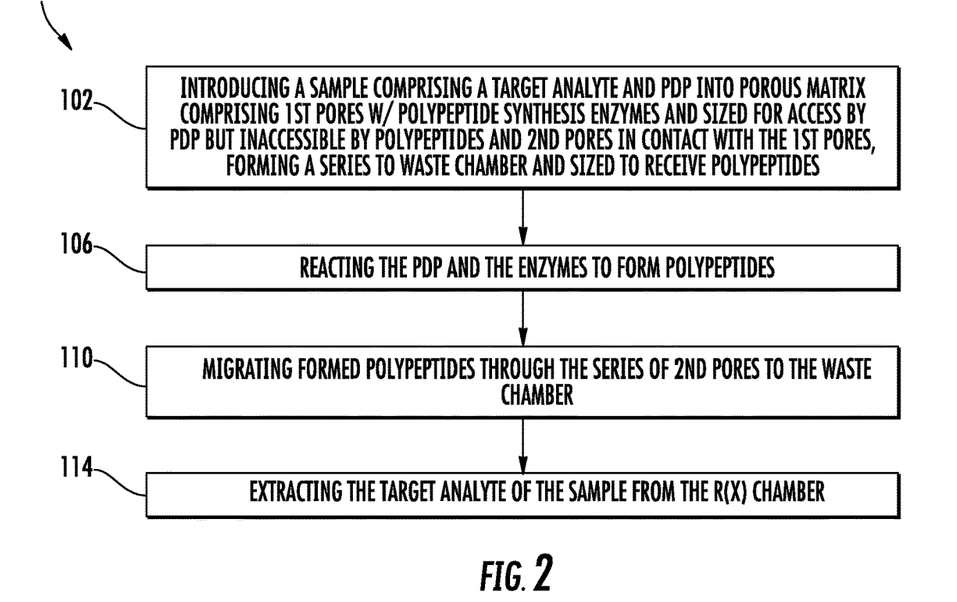
FIG. 2 is a flow diagram of an example enzymatic sample purification method.

Although FIG. 2 illustrates an example arrangement of pores 70 and pores 72 as well as example polypeptide passages 76, in other implementations, the exact arrangement of pores 70 and 72 may vary in numerous fashions. Polypeptide passages 76 may be longer, shorter, straighter or more serpentine than what is schematically illustrated. A polypeptide passage may have a width of multiple interconnected pores 72 at certain locations along its length. The number or density of polypeptide passages 72 within the volume of porous matrix 30 may be greater than that shown. The individual pores 70 and 72 may not have uniform shapes and/or sizes. Not all of the larger pores 72 may be connected to other adjacent pores 72. For example, individual larger pores 72 or small clusters of multiple pores 72 may be isolated within reaction chamber 24 from other larger pores 72 so as to not form part of a polypeptide passage connected to waste chamber 26.

Figure 3:
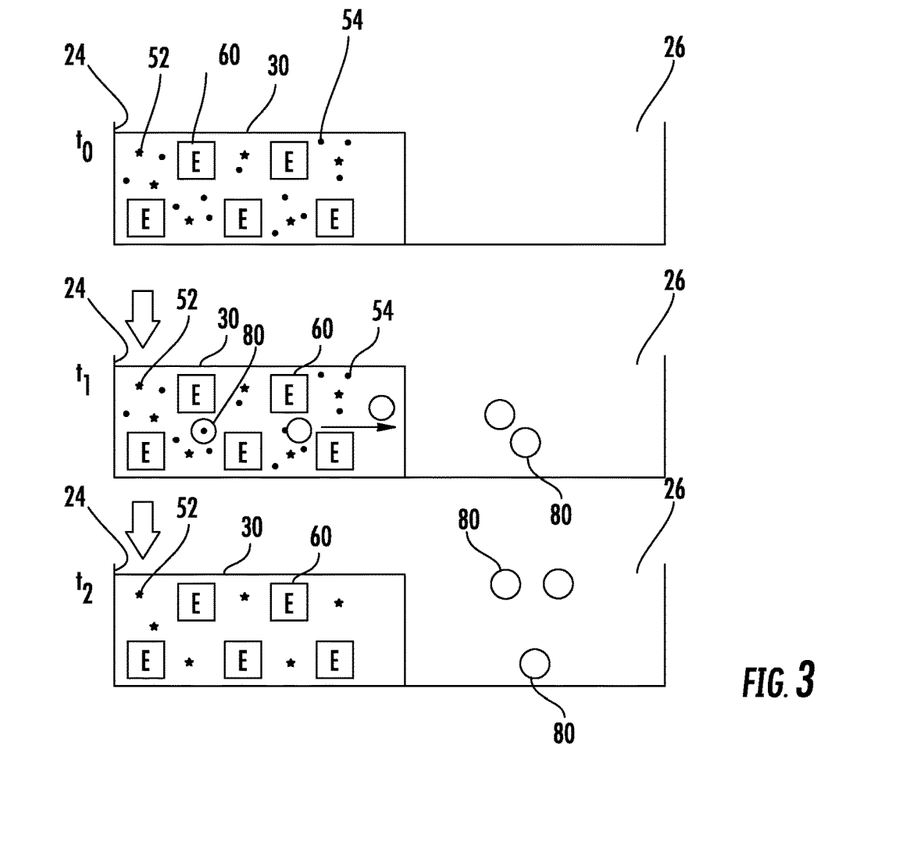
FIG. 3 is a diagram of an example enzymatic sample purification system carrying out the example method of FIG. 2.

FIG. 2 is a flow diagram of an example enzymatic sample purification method 100. FIG. 3 is a diagram schematically illustrating method 100 at different points in time. For purposes of illustration, porous matrix 30, enzymes 60 as well as analyte 52 and PDP 54 of sample 50 are schematically simplified in FIG. 3. Although method 100 is described as being carried out by system 20, method 100 may alternatively be carried out by any of the other enzymatic sample purification systems described hereafter or the other appropriate enzymatic sample purification systems. As indicated by block 102 and illustrated at time $t_0$ in FIG. 3, sample 50 is introduced through port 34 into reaction chamber 24. Sample 50 comprises target analyte 52 (schematically illustrated with stars) and PDP 54 (schematically illustrated as an amino acid with solid circles). Examples of sample 50 include, but are not limited to, blood, serum, sell lysate, extracellular fluid, milk and/or other biological fluids. Target analyte 52 may comprise small molecules that are unable to form peptide bonds (amide bonds). Such markets do not have primary and mine groups or carboxylic acid groups and are therefore, unable to form amide bonds.

Analyte 52 may additionally or alternatively comprise molecules that are able to form peptide bonds, but do not form peptide bonds under the enzymatic conditions present in reaction chamber 24 due to the particular enzyme 60 chosen or the other conditions of reaction chamber 24. Such molecules may have primary amine groups or carboxylic acid groups, but are unable to undergo peptide bond formation given the particular enzyme 60 within reaction chamber 24. Such an analyte may include amino acids or oligopeptides that are sterically excluded from the active site of the peptide forming enzyme. Examples of such analytes include, but are not limited to, biomarkers such as thyrotropin-releasing hormone (a tripeptide), Leu-enkephalin, Met-enkephalin (pentapeptides), and others. In one method, the analyte 52 and PDP 54 of sample 50, prior to purification, have molecular weights and radii of gyration that overlap or that are similar to make separation by size alone difficult. In addition, in some implementations, the molecules of analyte 52 and the molecules of PDP 54 may also have similar charge, electrophoretic mobility, partition coefficient (related to hydrophobicity), protein kinase A (pKa) properties, rendering ion selective, electrophoretic and/or liquid and solid-based separation difficult.

As further indicated by block 102, reaction chamber 24, into which sample 50 is deposited, contains enzymes (E) 60, an enzyme cofactor and a cosolvent. In one implementation, reaction chamber 24 additionally contains a buffer. Enzyme 60, the enzyme cofactor, the cosolvent and the buffer are each described above.

As indicated by block 106 and illustrated at time $t_1$, in FIG. 3, the enzyme 60 and the PDP 54 are allowed to react with one another to form polypeptides 80 (schematically illustrated with open circles). During such reactions, the PDP 54 of sample 50 accesses enzyme 60 within pores 70. This results in the formation of polypeptides 80. As schematically illustrated in FIG. 1, the polypeptides 80 have molecular sizes so as to fit within pores 72 and so as to be movable through and across pores 72, from one pore 72 into it an adjacent pore 72.

As indicated by block 110 and further illustrated at time $t_1$ in FIG. 3, the formed polypeptides 80 migrate or travel through polypeptide passages 76 (shown in 1) into waste chamber 26. Due to the molecular size differences between target analyte 52 and the formed polypeptides 80, the polypeptides 80 cannot access the smaller pores 70 and are contained within polypeptide passages 76, constraining movement of polypeptides 80 along more linear or direct paths towards waste chamber 26. In contrast, target analyte 52 may travel between and amongst each and every pore 70, possibly taking much longer and serpentine path within and throughout matrix 30. As a result, target analyte 52 is entropically trapped within matrix 30 and reaction chamber 24, traveling to waste chamber 26, if at all, at a much, much slower rate as compared to the formed polypeptides 80. Relative to polypeptides 80, target analyte 52 is entropically trapped within matrix 30 due to its smaller sized molecules.

In one implementation, the polypeptides 80 are at least 100 percent larger than target analyte 52. In one implementation, polypeptides 80 have a size of at least 1000 Da of the target analyte has a size of no greater than 200 Da.

The removal of the created polypeptides 80 from reaction chamber 24 inhibits attainment of an equilibrium state within reaction chamber 24 between polypeptides 80 and enzyme 60. As a result, a non-equilibrium state persists within reaction chamber 24 to enhance further reaction of enzyme 60 with PDP 54 to produce yet more polypeptide 70 which is also transported or which also migrates to waste chamber 26.

As indicated by block 114 and illustrated at time $t_2$ in FIG. 3, the process or cycle of reacting PDP 54 enzyme 60 to form polypeptides and continuously or simultaneously migrating form polypeptides 80 through passages 76 to chamber 26 is continued or repeated until the remaining sample 50 within reaction chamber 24 has achieved a predetermined level of purity, until the remaining PDP 54 in reaction chamber 24 has fallen to an acceptable level or amount. In one implementation, substantially all of the PDP 54 has been consumed as a result of reactions with enzyme 60 and subsequently removed in the form of polypeptides 80 transported to waste chamber 26. At completion of the process, target analyte 52 is extracted from reaction chamber 24 for further analysis.

Figure 4:
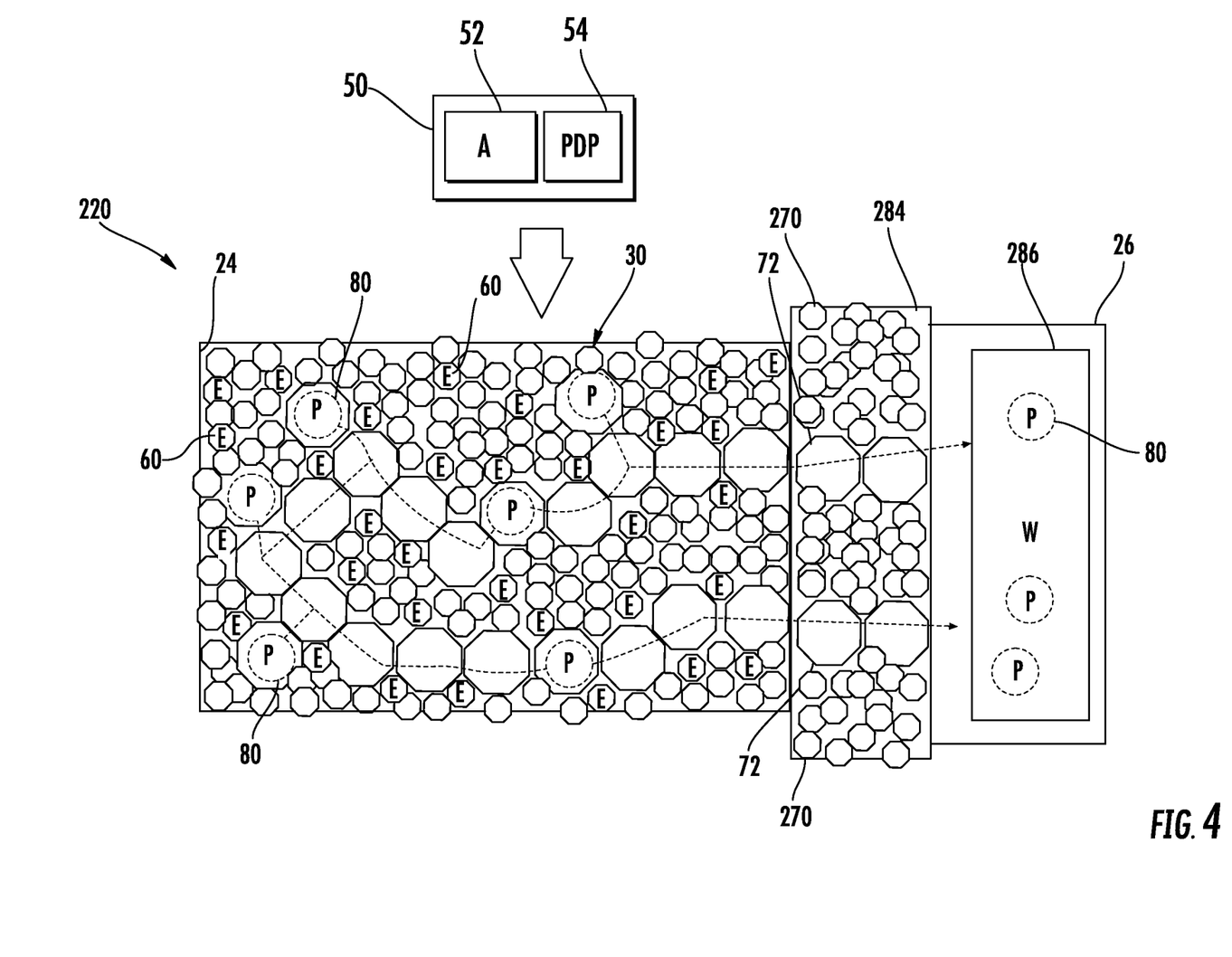
FIG. 4 is a schematic diagram of an example enzymatic sample purification system.

FIG. 4 schematically illustrates enzymatic sample purification system 220, an example implementation of system 20. System 220 is similar to system 20 except that system 220 additionally comprises partition 284 and buffer 286. Those remaining components or elements of system 220 which correspond to system 20 are numbered similarly.

Partition 284 comprises a filter or membrane sandwiched between reaction chamber 24 containing porous matrix 30 and waste chamber (W) 26. Partition 284 transmits polypeptides 80 to waste chamber 26 while blocking or inhibiting the flow of target analyte 52 of sample 50 to waste chamber 26. As shown by FIG. 4, in one implementation, partition 284 may have a construction similar to that of porous matrix 30 in that partition 284 comprises multiple differently sized pores. In one such implementation, partition 284 comprises larger pores 72 and smaller pores 270. Larger pores 72 are similar to pores 72 of matrix 30 in that larger pores 72 are sized to receive and permit passage of the formed polypeptides 80 resulting from the reaction of PDP 54 and enzymes 60 in reaction chamber 24. In one implementation, the smaller pores 270 are sized smaller than pores 70 so as to not only block the transmission of polypeptides 80, but also block the transmission of target analyte 52 such that target analyte 52 is not captured or contained within partition 284. In some implementations, pores 280 may be omitted, being replaced with a solid or otherwise imperforate layer or structure. In yet other implementations, pores 270 may be sized similar to pores 70, wherein target analyte 52 is allowed to enter such pores 270, but becomes entropically trapped within partition 284 prior to reaching waste chamber 26. In yet other implementations, partition 24 may have other forms that allow the transmission of polypeptides 80, but more greatly inhibit or restrict the flow of target analyte 52 as compared to the flow of polypeptides 80 through pores 72.

Buffer 286 comprises molecules that, as part of the solution in waste chamber 26, inhibit changes to the pH of the solution in waste chamber 26. Buffer 286 as chemical characteristics chosen so as to inhibit or prevent the breakdown of the form polypeptides 80 within waste chamber 26 so as to inhibit return floor back flow of PDP 54 into reaction chamber 24. Examples of buffers include, but are not limited to, phosphate buffer. In some implementations, buffer 286 may be omitted.

Figure 5:
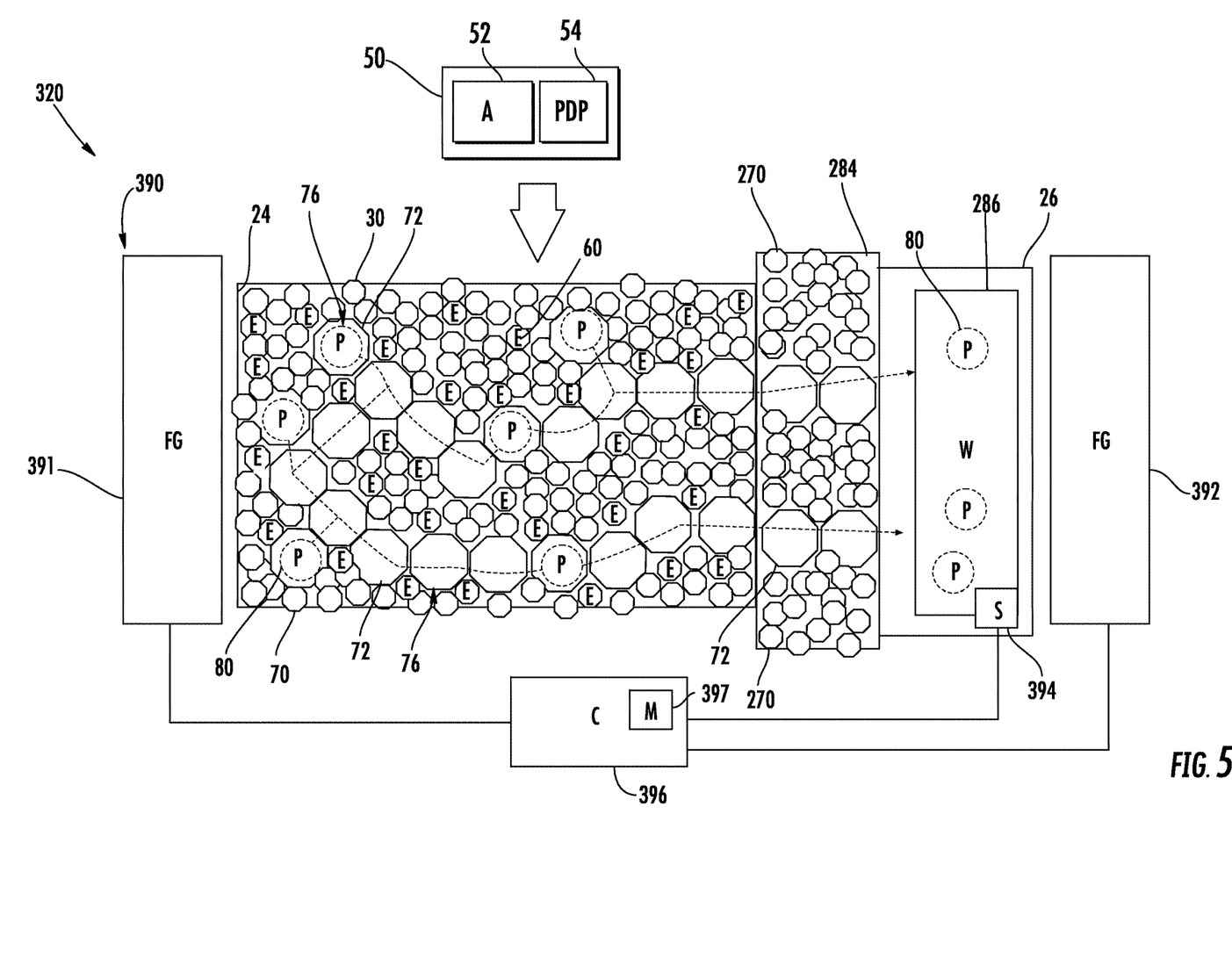
FIG. 5 is a schematic diagram of an example enzymatic sample purification system.

FIG. 5 schematically illustrates enzymatic purification system 320, another example implementation of system 20. System 320 is similar to system 220 described above except that system 320 additionally comprises field generation system 390. Those remaining components or elements of system 320 which correspond to components or elements of systems 20 and 220 are numbered similarly.

Field generation system 390 applies a field across porous matrix 30 so as to accelerate the transport, movement or migration of polypeptides 80 from reaction chamber 24 to waste chamber 26 through polypeptide passages 76. By accelerating the movement of polypeptides 80 out of reaction chamber 24, a higher state of non-equilibrium within reaction chamber 24 between the presence of polypeptides 80 and enzymes 60 may be achieved to enhance the reaction rate of PDP 54 with enzyme 60. Field generation system 390 comprises field generators 391, 392, sensor 394 and controller 396. Field generators 391, 392 comprise terminals between which the field that accelerates the transporter movement of polypeptides 80 is created. Field generators 391 determine the path and direction of the field as well as the path and direction of the accelerated movement of polypeptides 80.

In one implementation, field generators 391, 392 comprise nodes of an electric potential gradient field generator, wherein field generators 391, 392 are at two different electrical potentials, creating an electrical field through and across matrix 30 to bias or accelerate movement of polypeptides 80 from reaction chamber 24 to waste chamber 26. In one such implementation, the electric field moves polypeptides 80 by electrophoresis. In another such implementation, the electric field moves polypeptides 80 by electroosmosis. In one implementation, field generators 391, 392 comprise nodes of a thermal gradient field generator, wherein field generators 391, 392 are at different temperatures, creating a thermal gradient through and across matrix 30 to bias or accelerate movement of polypeptides 80 from reaction chamber 24 to waste chamber 26. In yet another implementation, field generators 391 and 392 comprise nodes of a pressure gradient field generator, wherein field generators 391, 392 are different fluid pressure levels to create a fluid pressure differential across and through matrix 30 to move polypeptides 80 towards and into waste chamber 26. In yet other implementations, other field generators may be employed to bias or accelerate the movement or migration of polypeptides 80 towards waste chamber 26.

In those implementations that employ field generation system 390, the strength or amount of the bias provided by field generators 391, 392 is selected so as to be strong enough to accelerate the movement of polypeptides 80 through polypeptide passages 76 out of reaction chamber 24 and into waste chamber 26 while not being so strong so as to also drive target analyte 52 at a rate such that the movement of target analyte 52 overcomes the entropic trapping or retention of analyte 52 by the more numerous smaller pores 70 and also be discharged to waste chamber 26. The exact strength of the field provided by field generation system 390 may vary and may be empirically determined depending upon the ease at which target analyte 52 may move through porous matrix 30 which may depend upon the relative sizes of pores 70, 72, the number and sizes of pores 70, the density of pores 70, the density of pores 72, the density of polypeptide passages 76 and the size or affinities of target analyte 52 to the material matrix 30.

In the example illustrated, sensor 394 and controller 396 of system 390 provide closed-loop feedback control of the field being provided by field generators 391, 392. Sensor 394 comprises a device that senses or detects properties of the solution within waste chamber 26.

Controller 396 comprises a processing unit that, following instructions contained in a non-transitory computer readable medium 397, adjusts the field being applied across matrix 30 by field generator 391, 392 based on signals or sensed values received from sensor 394. For purposes of this application, the term "processing unit" shall mean electronics or hardware that executes sequences of instructions contained in a non-transitory memory. Execution of the sequences of instructions causes the processing unit to perform steps such as generating control signals. The instructions may be loaded in a random access memory (RAM) for execution by the processing unit from a read only memory (ROM), a mass storage device, or some other persistent storage. In other embodiments, hard wired circuitry may be used in place of or in combination with software instructions to implement the functions described. For example, controller 396 may be embodied as part of one or more application-specific integrated circuits (ASICs). Unless otherwise specifically noted, the controller is not limited to any specific combination of hardware circuitry and software, nor to any particular source for the instructions executed by the processing unit.

In one implementation, sensor 394 senses the presence of polypeptides 80, wherein the number, amount or other sensed value of the polypeptides 80 is transmitted to controller 396, wherein controller 396 uses the sensed value of polypeptides 80 to adjust the field that biases movement of polypeptides 80. For example, if signals from sensor 394 indicate a slow rate of increase of polypeptides 80 within waste chamber 286, controller 396 may output signals strengthening the field provided by field generators 391, 392. Conversely, if the signals from sensor 394 indicate a high rate of increase of the number, amount or percentage of polypeptides 80 within waste chamber 286 to such an extent that there may be a high likelihood that target analyte 52 is also being transported to waste chamber 26, controller 396 may output control signals reducing the field provided by field generators 391, 392.

In another implementation, sensor 394 may sense the presence of molecules other than polypeptides 80, the presence of biomarkers and/or the presence of target analyte 52 within waste chamber 26, wherein controller 396 uses the sensed value to adjust the field that biases movement of polypeptides 80. For example, if signals from sensor 394 indicate an amount, percentage, volume or other value of non-polypeptide molecules, biomarkers and/or target analyte 52 in waste chamber 26 and wherein the value exceeds the predetermined threshold, controller 396 may automatically lessen or reduce the field provided by generator 391, 392 so as to reduce the likelihood that the target analyte 52 also be transported or biased into waste chamber 26. Conversely, if signals from sensor 394 indicate an amount, percentage, volume or other value of non-polypeptide molecules, biomarkers and/or target analyte 52 in waste chamber 26 and wherein the value is below a predetermined threshold, controller 396 may automatically increase the field provided by generators 391, 392 so as to increase the rate at which polypeptides 80 migrate to waste chamber 26 and thereby increase the rate at which sample 50 is purified. Such predetermined thresholds may be empirically determined and may vary depending upon the ease at which target analyte 52 may move through porous matrix 30 which may depend upon the relative sizes of pores 70, 72, the number and sizes of pores 70, the density of pores 70, the density of pores 72, the density of polypeptide passages 76 and the size or affinities of target analyte 52 to the material matrix 30.

Although the present disclosure has been described with reference to example implementations, workers skilled in the art will recognize that changes may be made in form and detail without departing from the spirit and scope of the claimed subject matter. For example, although different example implementations may have been described as including one or more features providing one or more benefits, it is contemplated that the described features may be interchanged with one another or alternatively be combined with one another in the described example implementations or in other alternative implementations. Because the technology of the present disclosure is relatively complex, not all changes in the technology are foreseeable. The present disclosure described with reference to the example implementations and set forth in the following claims is manifestly intended to be as broad as possible. For example, unless specifically otherwise noted, the claims reciting a single particular element also encompass a plurality of such particular elements. The terms "first", "second", "third" and so on in the claims merely distinguish different elements and, unless otherwise stated, are not to be specifically associated with a particular order or particular numbering of elements in the disclosure.

What is claimed is:

1. An enzymatic sample purifier comprising:
a waste chamber;
a reaction chamber having a port to receive a sample comprising a protein degradation product (PDP), and the reaction chamber containing a polypeptide synthesis enzyme, an enzyme cofactor, and a cosolvent, wherein polypeptides are formed in the reaction chamber when the sample is received in the reaction chamber and reacts with the polypeptide synthesis enzyme; and
a porous matrix within the reaction chamber, wherein the porous matrix comprises first pores having a first size and second pores having a second size larger than the first size, the first size being smaller than a molecular size of the polypeptides, the second pores being larger than the molecular size of the polypeptides, in contact with the first pores and forming a polypeptide passage comprising a series or chain of the second pores, wherein the polypeptide passage extends from within the reaction chamber to the waste chamber.

2. The enzymatic sample purifier of claim 1, wherein the first pores comprise at least 10% and no greater than 95% of the porous matrix.

3. The enzymatic sample purifier of claim 1, wherein the first pores comprise at least 80% and no greater than 95% of the porous matrix.

4. An enzymatic sample purifier comprising:
a waste chamber;
a reaction chamber containing a polypeptide synthesis enzyme, an enzyme cofactor and a cosolvent, the reaction chamber having a port to receive a sample comprising a protein degradation product (PDP), and polypeptides are formed in the reaction chamber when the sample is received in the reaction chamber and reacts with the polypeptide synthesis enzyme;
a porous matrix within the reaction chamber, wherein the porous matrix comprises first pores having a first size and second pores having a second size larger than the first size, the first size being smaller than a molecular size of the polypeptides, the second pores being larger than the molecular size of the polypeptides, in contact with the first pores, and forming a polypeptide passage comprising a series or chain of the second pores, wherein the polypeptide passage extends from within the reaction chamber to the waste chamber; and
a field generator to apply a field to accelerate transport of the formed polypeptides through the second pores to the waste chamber.

5. The enzymatic sample purifier of claim 4, wherein the field generator is selected from a group of field generators consisting of: an electric potential gradient field generator, a thermal gradient field generator, an osmotic gradient field generator and a pressure gradient field generator.

6. An enzymatic sample purifier comprising:
a waste chamber;
a reaction chamber containing a polypeptide synthesis enzyme, an enzyme cofactor and a cosolvent, the reaction chamber having a port to receive a sample comprising a protein degradation product (PDP), and polypeptides are formed in the reaction chamber when the sample is received in the reaction chamber and reacts with the polypeptide synthesis enzyme;
a porous matrix within the reaction chamber, wherein the porous matrix comprises first pores having a first size and second pores having a second size larger than the first size, the first size being smaller than a molecular size of the polypeptides, the second pores being larger than the molecular size of the polypeptides, in contact with the first pores, and forming a polypeptide passage comprising a series or chain of the second pores, wherein the polypeptide passage extends from within the reaction chamber to the waste chamber; and
a buffer within the waste chamber to inhibit polypeptide breakdown.

7. The enzymatic sample purifier of claim 6 further comprising a partition between the reaction chamber and the waste chamber, the partition being permeable to molecules greater than the first size and impermeable to molecules less than the first size, wherein the partition omits the polypeptide synthesis enzyme.

8. The enzymatic sample purifier of claim 6, wherein the polypeptide passage carries the polypeptides to the waster chamber, and does not carry a target analyte retained in the first size pores.

9. The enzymatic sample purifier of claim 8, comprising:
a persistent non-equilibrium state in the reaction chamber between the polypeptides and the polypeptide synthesis enzyme, wherein the persistent non-equilibrium state causes additional polypeptides to be formed in the reaction chamber and expelled through the polypeptide passage to the waste chamber.

10. The enzymatic sample purifier of claim 9, wherein the additional polypeptides are formed in the reaction chamber and expelled through the polypeptide passage to the waste chamber over a plurality of cycles.

11. The enzymatic sample purifier of claim 1, wherein the reaction chamber comprises serpentine paths formed from the first pores, and the serpentine paths are longer than the polypeptide passage formed from the second pores.

12. The enzymatic sample purifier of claim 11, wherein an amount of first pores is greater than an amount of second pores in the reaction chamber.

13. The enzymatic sample purifier of claim 11, comprising:
   a field generator to apply a field to accelerate transport of the formed polypeptides through the second pores to the waste chamber.

14. The enzymatic sample purifier of claim 13, wherein the field generator is selected from a group of field generators consisting of: an electric potential gradient field generator, a thermal gradient field generator, an osmotic gradient field generator and a pressure gradient field generator.

15. The enzymatic sample purifier of claim 11, comprising:
   a buffer within the waste chamber to inhibit polypeptide breakdown.

16. The enzymatic sample purifier of claim 1, comprising:
   a partition between the reaction chamber and the waste chamber, the partition being permeable to molecules greater than the first size and impermeable to molecules less than the first size, wherein the partition omits the polypeptide synthesis enzyme.

\* \* \* \* \*